United States Patent [19]

Seitz et al.

[11] Patent Number: 5,015,843

[45] Date of Patent: May 14, 1991

[54] FIBER OPTIC CHEMICAL SENSORS BASED ON POLYMER SWELLING

[75] Inventors: William R. Seitz, Durham, N.H.; Marian F. McCurley, Watertown, Mass.

[73] Assignee: Polysense, Inc., Wellesley, Mass.

[21] Appl. No.: 480,548

[22] Filed: Feb. 15, 1990

[51] Int. Cl.$^5$ ................................. H01J 5/16
[52] U.S. Cl. ........................... 250/227.21; 250/231.1
[58] Field of Search ...................... 250/227.11, 227.21, 250/231.1, 227.24

[56] References Cited

U.S. PATENT DOCUMENTS

| | | | |
|---|---|---|---|
| 4,645,923 | 2/1987 | De Blok et al. | 250/227.24 |
| 4,749,856 | 6/1988 | Walker et al. | 250/227.11 |
| 4,915,473 | 4/1990 | Haese et al. | 250/227.14 |
| 4,934,811 | 6/1990 | Watts | 250/227.11 |

OTHER PUBLICATIONS

Seitz, CRC Critical Review in Analytical Chemistry (1988), vol. 19, Iss. 2, pp. 135-173.
Kawahara, Analytica Chimica Acta, (1983), 151, pp. 315-325.
Sutherland, Analytical Letters, (1984), 17(B1), pp. 43-53.
Giuliani, Sensors and Actuators, (1984), 6, pp. 107-112.
Butler, Appl. Phys. Lett. (1984), 45, pp. 1007-1009.
Dessy, Analytical Chemistry, (1985), 57, pp. 1188-1202.
Giuliani, Optics Letters (1983), 8, pp. 54-56.
Goldfinch, Analytical Biochemistry (1984), 138, pp. 430-436.
Goldfinch, Analytical Biochemistry (1980), 109, pp.216-221.
Freeman, Analytica Chimica Acta (1985), 177, pp. 121-128.
Smith, Applied Spectroscopy (1988), 42, pp. 1469-1472.
Pawliszyn, Rev. Sci. Instrum. (1987), 58, pp. 245-248.
Ansorge, Exp. Cell Res. (1982), 140, pp. 31-37.
Miller, Am. Biotechnol. Lab. (1989), Jan. pp. 30-37.
Flory, Principles of Polymer Chemistry (1953), pp. 576-589.
Guillot, Future Directions in Polymer Colloids (1987), pp. 65-77.
Katchalsky, J. Polymer, Sci. (1951), 7.
Zhujun, Analytical Chemistry (1989), 61, pp. 202-205.
Dowling, Macromoleculs (1986), 19, pp. 344-347.
Martell, Critical Stability Constants, vol. 1, pp. 199-202.
Feigenbaum, J. Poly. Sci. (1971), 9, pp. 817-820.
Ungaro, Journal of the Am. Chem. Soc., (1976), pp. 5198-5202.
Sen, Chem. Rev. (1985), 85, pp. 271-281.
Bender, Cyclodextrin Chemistry (1978), pp. 10-21.
Cramer, Chemische Berichte Jahrg. 90 (1957), pp. 2561-2571.
Solms, Helvetica Chimica Acta (1965), 48, pp. 1225-1228.
Hoffman, Macromol. Sci.-Chem. (1973), A7(5), pp. 1147-1157.
Turner, The Swelling of Polymer Gels (1988), pp. 40-43.
Kissinger, Measurements & Control, Apr. 1988.
Gilbert, Analytical Chemistry (1073), 45, pp. 1390-1393.
Dorsey, Analytical Chemistry (1978), 50, pp. 1330-1333.
Osada, Advances in Polymer Science 82, Springer-Verlag Berlin Heidelberg (1987) pp. 1-46.
Kost et al., J. Biomedical Materials Research, (1985) vol. 19, pp. 1117-1133.

*Primary Examiner*—David C. Nelms
*Assistant Examiner*—Stephone B. Allen

[57] ABSTRACT

Chemical sensors can detect the presence of chemical species in solution based upon polymer swelling in response to the chemical species. Polymer swelling is indirectly determined by measuring light reflected from a reflector affixed directly or indirectly to the polymer. Such that increase or decrease in the size of the polymer changes the distance between the reflector and a light source. Measurements of the light reflected from the reflector indicate the amount of swelling or shrinkage of the polymer in response to the chemical species.

30 Claims, 5 Drawing Sheets

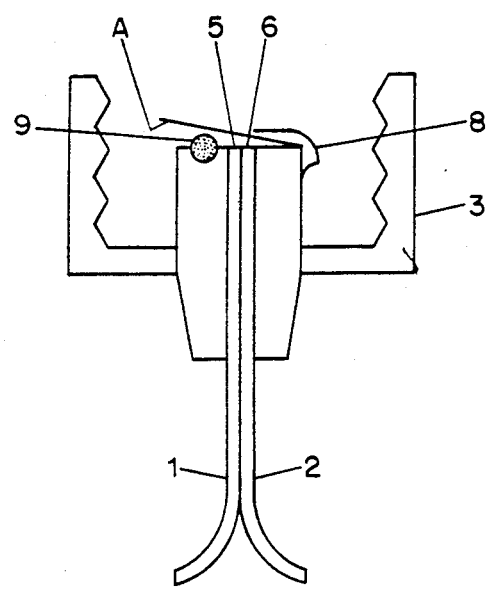
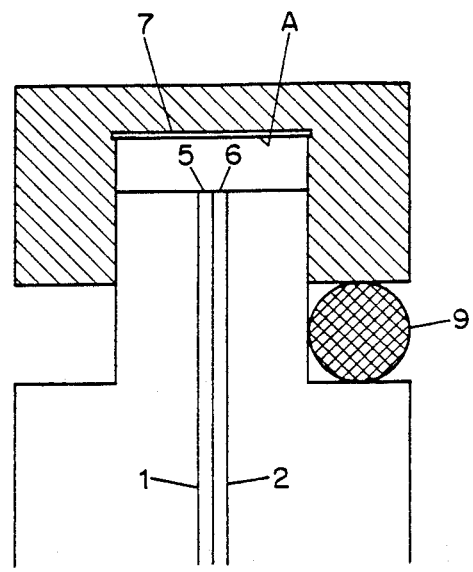
FIG. 1
FIG. 2
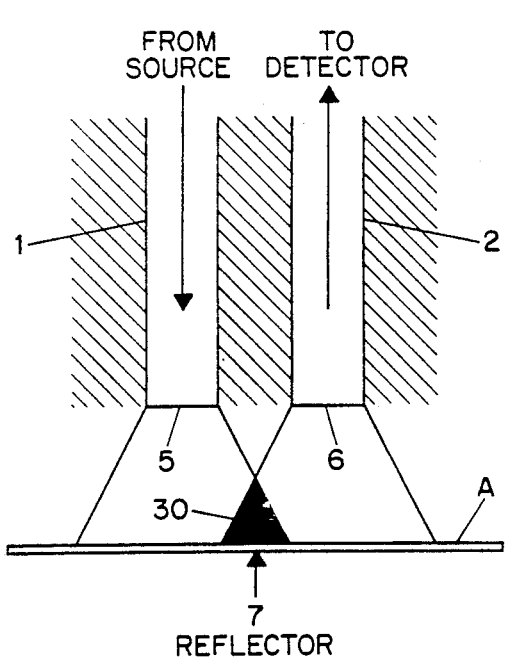
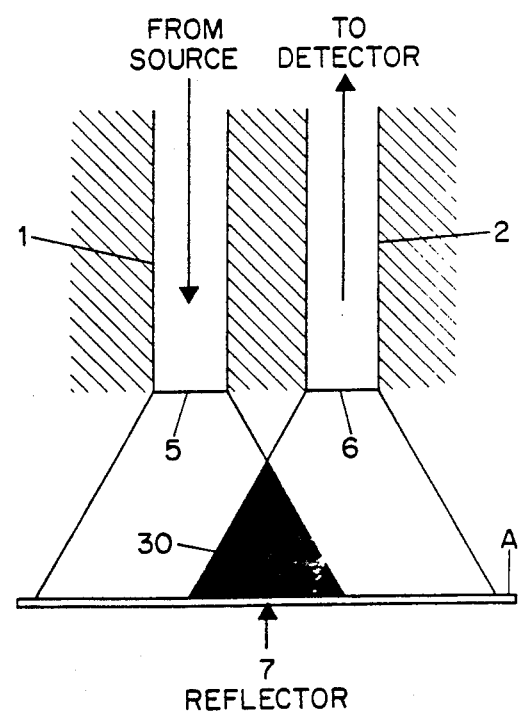
FIG. 3a
FIG. 3b

FIBER OPTIC CHEMICAL SENSORS BASED ON POLYMER SWELLING

BACKGROUND OF THE INVENTION

This invention relates to fiber optic chemical sensors which indicate the presence of chemical species in solution based upon polymer swelling.

Sensors for chemical species of a variety of types are known, including many which rely on optical detection. For example, detection systems which rely on the absorbance, emission or scattering of light are known.

In recent years, sensors which incorporate fiber optics to transport light between the sample and a light source or sensor have been proposed. See Seitz, "Chemical Sensors Based on Immobilized Indicators and Fiber Optics," CRC Crit. Rev. Anal. Chem. 19, 135 (1988) and references cited therein. These systems frequently rely upon the visible or near ultraviolet spectral characteristics of a chemical species formed by reaction of an indicator reagent with the analyte. This design choice, however, gives rise to several disadvantages.

First, the wavelengths of light used in these devices are not well transmitted due to the absorption properties of the optical fibers. This can lead to a loss of sensitivity. Further, sensor stability is generally limited by the indicator. Since the sensing mechanism requires photoexcitation, photodecomposition is often a problem. It tends to become an even more serious problem when sensors are miniaturized since a relatively larger amount of light has to be directed into the indicator to maintain signals at a level where they can be measured with adequate precision. Many of the indicators are dyes originally designed for use in solution measurements on a onetime basis, an application that does not require nearly as high intrinsic stability as sensing. As a consequence many of the indicator dyes are not particularly stable.

There are also a limited number of chemical sensor applications involving optical processes other than absorption or luminescence. Chemical sensing has been based on changes in fiber transmission accompanying changes in the refractive index at the surface of the fiber core. Kawahara et al., "Development of a Novel Method for Monitoring Oils in Water", Anal. Chim. Acta, 151, 315 (1983); Sutherland et al., "Preliminary Results Obtained With a No-Label Homogeneous, Optical Immunoassay For Human Immunoglobulin G", Anal. Lett., 17, 43 (1984); and Guiliani et al., "Detection of Simple Alkanes at a Liquid-Glass Interface by Total Internal Optical Scattering", Sensors and Actuators, 6, 107 (1984). The feasibility of interferometric chemical sensing has also been demonstrated. Butler, "Optical Fiber Hydrogen Sensor", Appl. Phys. Lett; 45, 1107 (1984); and Dessy, "The Electronic Toolbox I", Anal. Chem., 57, 1188A (1985). Interaction of the analyte with an indicator phase coated around the core of a fiber constricts the fiber causing a change in the phase of the light transmitted through the fiber. This type of sensor can be extremely sensitive provided it is kept in a protected environment which minimizes the effects of vibration and temperature.

Most fiber optic chemical sensors reported to date use conventional spectroscopic instrumentation. The detector is most frequently a photomultiplier tube, although photodiodes are also common. The sources are usually a tungstenhalogen lamp, a xenon arc lamp or a laser, usually an argon ion laser. Sensor systems using continuum sources generally require a filter or a monochromator for wavelength resolution.

Light emitting diodes (LEDs) have been used in only a few sensors. Guiliani et al., "Reversible Optical Waveguide Sensors for Ammonia Vapors", Optics Lett., 8, 54 (1983); Goldfinch et al., "Solid-phase Optoelectronic Sensors for Biochemical Analysis", Anal. Biochem., 138, 430 (1984); Goldfinch et al., "A Solid-phase Optoelectronic Sensor for Serum Albumin", Anal. Biochem., 109, 216 (1980); and Freeman et al., "A Fiber-Optic Absorption Cell for Remote Determination of Copper in Industrial Electroplating Baths", Anal. Chem. Acta, 177, 121 (1985). The infrequent use of LEDs is due to the fact that they are only available at relatively long wavelengths and thus are not compatible with many indicators. An LED which emits blue light is available, but it has a very wide emission band and is considerably less intense than longer wavelength LEDs. Where applicable, LEDs are attractive sources. In addition to their low cost, long wavelength LEDs emit a relatively narrow band of light and thus do not require wavelength resolution. Furthermore, if they are maintained at a constant temperature, LEDs are extremely stable light sources after they have been "burned in" for several days. Smith et al., "High Precision Fluorimetry with a Light Emitting Diode Source", Appl. Spec., 42, 1469 (1988); and Pawliszyn, "LEDs and Laser Diodes in Schlieren Optics Methods', Rev. Sci. Instrum., 58, 245 (1987). Temperature control is important since LED emission intensities change by about 0.5% per degree Celsius.

It is an object of the present invention to provide a class of sensor devices which use a light transmission means such as fiber optics in combination with an LED or other light source to provide accurate and specific detection of a variety of chemical species in solution.

SUMMARY OF THE INVENTION

Chemical sensors in accordance with the present invention use a light transmission means such as one or more optical fibers, a reflective member and a polymeric detector element which changes in volume in response to the presence of a particular analyte. In a two fiber device, the optical fibers are disposed in a housing such that light passing through a first of the optical fibers impinges on the reflective member and is reflected toward the second optical fiber. The second optical fiber collects at least a portion of the reflected light and transmits it to a device, such as a photodiode, for quantifying the amount of light collected by the second optical fiber. Single fibers transmitting light in both directions can also be employed. Additional fibers may also be advantageously incorporated, for example to provide for intensity ratioing.

The polymeric detector element is disposed between the reflective member and the housing in such a way that the position of the reflective member relative to the light transmission means will vary as a function of the volume of the polymeric detector element. The polymeric detector element need not be in direct contact with the housing or the reflective member, so long as there is mechanical coupling so that polymer swelling will cause a change in relative position. By selecting a polymeric detector element which swells or contracts in response to a particular chemical species, sensors that are specific to a wide variety of chemical species can be prepared.

BRIEF DESCRIPTION OF THE DRAWINGS

FIG. 1 shows an optical fiber sensor in accordance with the invention;

FIG. 2 shows an optical fiber sensor in accordance with the invention;

FIG. 3 depicts the dispersion of light in a sensor such as that shown in FIG. 2;

DETAILED DESCRIPTION OF THE INVENTION

Figure 4:
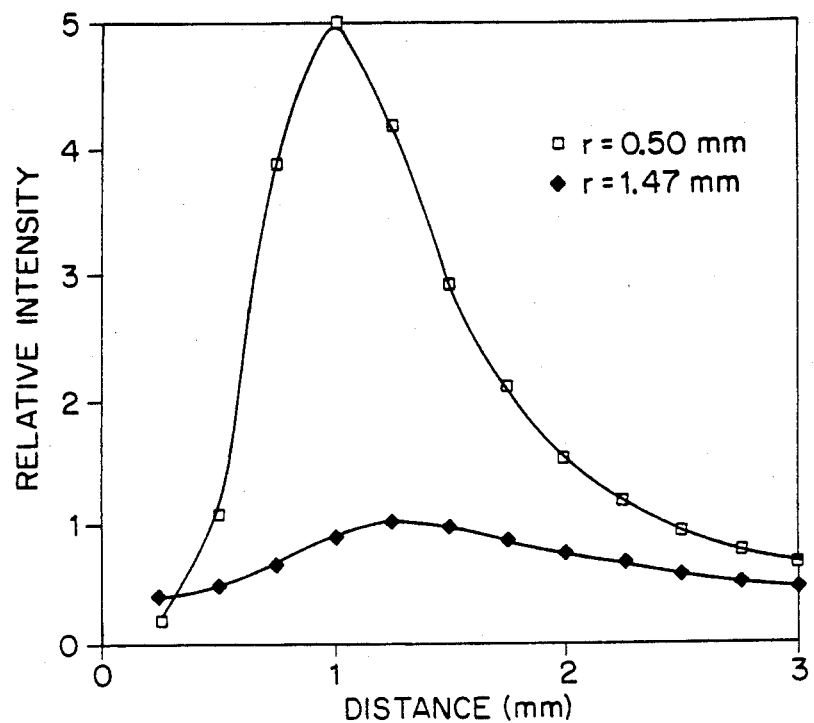
FIG. 4 shows the relationship between intensity and the distance between the reflective surface and the optical fibers in two sensors according to the invention.

FIG. 1 shows a first embodiment of the invention. In FIG. 1, two optical fibers 1,2 are disposed within a housing 3 such that an end surface 5,6 of each optical fiber 1,2 is exposed. A reflective member 7 is attached to the housing with an elastomeric hinge 8 (made, for example, of bathtub caulk) such that the reflective surface A points toward the ends 5,6 of the optical fibers 1,2. A polymeric detector element 9 is disposed between the housing 3 and the reflective member 7.

In use, light is supplied through optical fiber 1 (or 2), impinges on reflective surface A of reflective member 7 and is reflected toward end 6 (or 5) of optical fiber 2 (or 1). At least a part of this reflected light is collected by optical fiber 2 (or 1) and transmitted to a device for quantifying the amount of light collected.

The device depicted in FIG. 1 is capable of detecting the presence of an analyte in a sample if the polymeric detector element 9 is made from a material which undergoes a volume change in the presence of the analyte. Such a volume change of the polymeric detector element 9 alters the position of the reflective member 7 relative to the ends 5,6 of the optical fibers 1,2, and thus alters the amount of reflected light which is collected because the angle of incidence of the light on reflective surface A is changed.

FIG. 2 shows a second embodiment of the invention in which the reflective surface A remains at a constant angle to the ends 5,6 of the optical fibers 1,2. In this case, the reflective member 7 is deployed parallel to the ends 5,6 of the optical fibers 1,2, and the distance between reflective member 7 and the ends 5,6 changes in response to volume changes in the polymeric detector element 9.

In the embodiment of FIG. 2, the amount of light collected by optical fiber 2 (or 1) varies with the swelling of the bead because of the dispersion of the light is directly related to the distance between the reflective surface and the fiber ends. As shown in FIG. 3, the distance between the reflective surface A of the reflective member 7 controls the amount of light that is reflected into the end 6 (or 5) of the optical fiber 2 (or 1). Comparing FIG. 3(a) with FIG. 3(b) it can be seen that the amount of light collected 30 by fiber 2 (or 1) is directly related to the distance between the fiber ends 5, 6 and the reflective member 7. Such that the amount of light collected 30 increases with increasing distance between the fiber ends 5, 6 and the reflective member 7.

As will be apparent from a consideration of FIG. 3, the distance between the reflective surface and the ends of the optical fibers has a significant impact on the functioning of the device. In fact, the response function for the sensor will depend on a number of details of the optical arrangement, including: (1) the distance between the reflecting surface and the two fibers; (2) the distance between the two fibers; and (3) the angles of the cones of light emitted by the source fiber and accepted by the detector fiber. These angles depend both on the numerical aperture of the fiber and the refractive index of the measurement medium. To optimize sensor response, it is important to know how intensity depends on these variables.

The effect of the distance between the reflecting surface and the fiber ends can be modeled experimentally. Two optical fibers are held together such that the fiber ends are in the same plane. Light is introduced through one fiber. Intensity is detected through the other fiber as a function of the distance of a reflecting surface from the fiber ends. FIG. 4 shows data for two different displacements between the ends of the fiber. When the reflecting surface is very close, intensity increases as the reflecting surface moves away from the ends of the fibers because there is greater overlap between the cone of light emitted by the source fiber and the cone of light accepted by the detector fiber. Intensity goes through a maximum and then decreases with increasing distance. In this domain, intensity decreases because the light is more spread out at greater distances such that less can be collected by the fiber leading to the detector.

It is important to note that the position of the intensity maximum varies with distance between the fibers. For example, in the data of FIG. 4, there is a large change in the ratio of reflected intensities for the two displacements for reflector distances between 1.00 and 1.25 millimeters. This means that the proposed sensor can be implemented in an intensity ratio configuration. This involves using two detection fibers at different distances from the source fiber such that their intensity-vs.-reflector-position characteristics differ. Such a device could involve two optical fibers in which one transmits light in both directions or three separate fibers. Alternatively, fibers at different distances from the reflector or fibers of different light collection diameters or efficiencies could be employed. The intensity ratio measurement is insensitive to source fluctuations, intensity loss due to fiber bending and other parameters that affect single intensities.

Figures 5, 6:
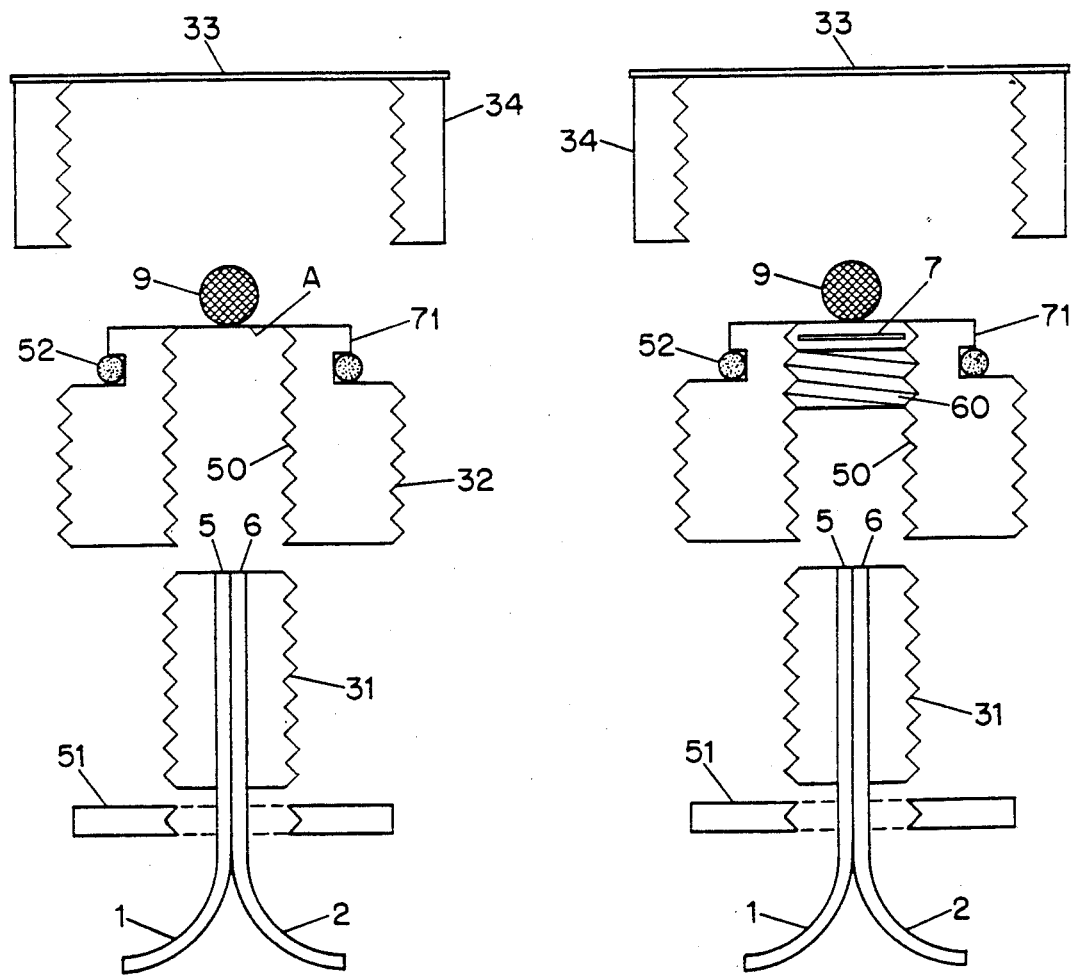
FIG. 5 shows an optical fiber sensor in accordance with the invention.
FIG. 6 shows an optical fiber sensor in accordance with the invention.

FIG. 5 shows a further embodiment of the sensor of the invention in which the reflective surface A does not come in contact with the sample. In FIG. 5, the housing is separable into three portions, a fiber optic support portion 31 which engages with one end of a bore 50 in middle portion 32 to define the distance between the ends 5,6 of the optical fibers 1,2 and the reflective surface A. The reflective surface A is part of a flexible membrane 71 which is disposed across the opposite end of the bore 50. The polymeric detector element 9 sits on top of this membrane 71 and is held in place by a ridig screen 33, which is part of the top portion 34 of the housing, when the top portion 34 is engaged with the middle portion 32. Finally, FIG. 5 shows a locking nut 51 to lock the fiber optic support portion 31 in one position and an O-ring 52 to prevent leakage of fluids through the joint formed by the middle portion 32 and top portion 34 of the housing.

In use, when the three parts of the housing are engaged, for example via threaded connectors as shown in FIG. 5, the sample will infiltrate through the rigid screen 33 and come in contact with the polymeric detector element 9. Swelling of the polymeric detector element 9 in response to the presence of an analyte will cause the flexible membrane 71 to deform downwards.

FIG. 6 shows a variation on the sensor device shown in FIG. 5. In FIG. 6, the reflective member 7 is separate from the flexible membrane 71 and is held in place against the flexible membrane 71 by a spring 60.

In making the sensors depicted in FIGS. 1, 2, and 5 and other sensors in accordance with the invention, it is preferred that the polymer bead be fixed in position relative to the housing, i.e., fixed to the housing or to a piece that is mechanically coupled to the housing. This can be accomplished by providing a depression on the surface of the housing (as shown in FIG. 1), using adhesives such as epoxies, white glue and caulking materials, or by covalently bonding the polymeric detector element in place.

Figure 7:
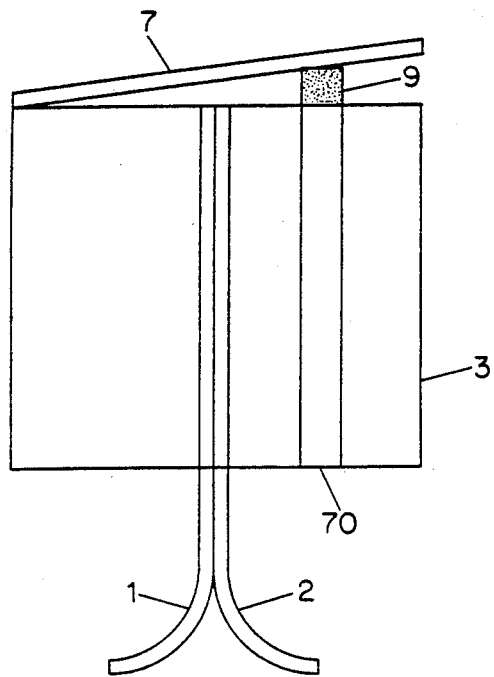
FIG. 7 shows an optical fiber sensor in accordance with the invention.

FIG. 7 shows an arrangement that can be used to facilitate covalent bonding. In FIG. 7, the optical fibers are epoxied in place in a small hole in the center of a housing 3 which is made of Teflon ®, Nylon ®, aluminum or some other machinable material. A short length of fused silica optical fiber 70 is inserted through a second hole in the side of the cylinder. The fused silica optical fiber 70 on the side of the housing 3 serves only as a polymer support and doesn't conduct any light. After etching with HF to roughen the surface, the end of the silica fiber is chemically treated to introduce surface functional groups that will covalently bond to the polymer sensing element. The specific chemistries vary according to polymer system employed.

Figure 8:
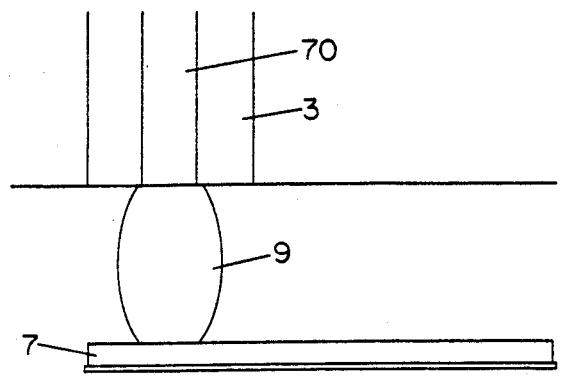
FIG. 8 shows a portion of an optical fiber sensor in accordance with the invention.

The polymer systems preferred for use in the invention share the common feature that they can be manipulated as liquids prior to solidifying. Immediately after combining the appropriate reagents for polymer formation, a drop of the material can be transferred to the sensor, thereby defining the size of the bead by the drop size. For example, the drop may be transferred onto the etched and chemically modified end of the fused silica optical fiber. Further, if bonding to the reflective surface is also desired, this fiber can be inverted and placed in contact with an appropriate chemically modified surface of the reflector as shown in FIG. 8. The distance between the fused 70 silica optical fiber and reflector will determine the shape of the polymer as it solidifies.

Figure 9:
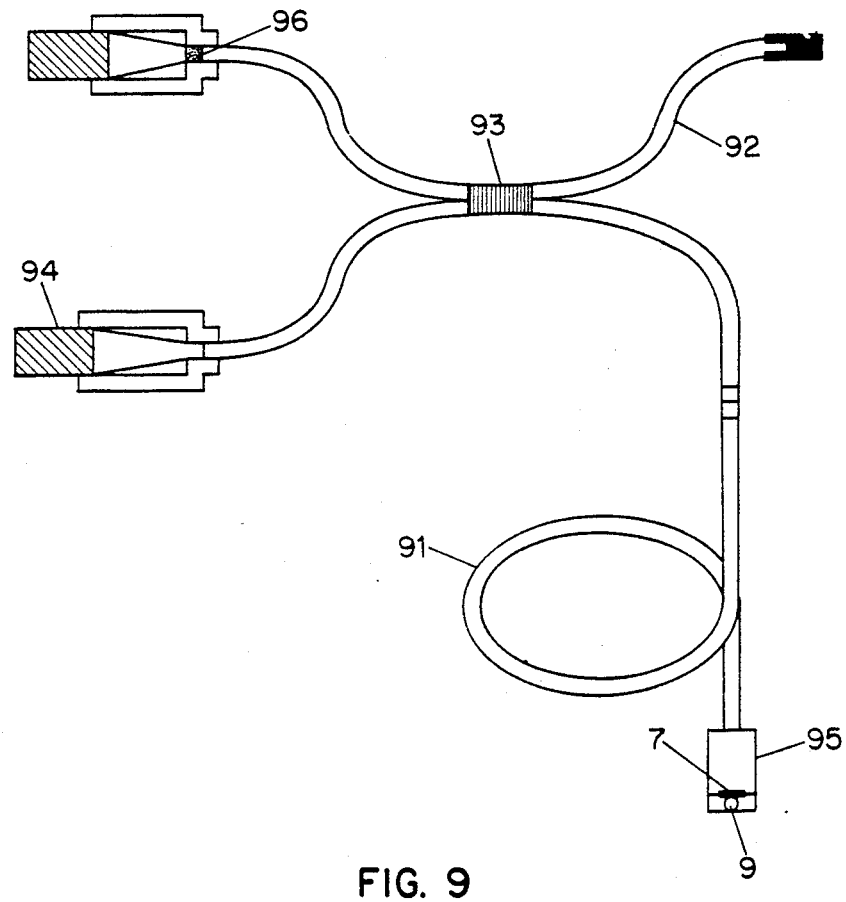
FIG. 9 shows an optical sensor in accordance with the invention.
Figure 10A:
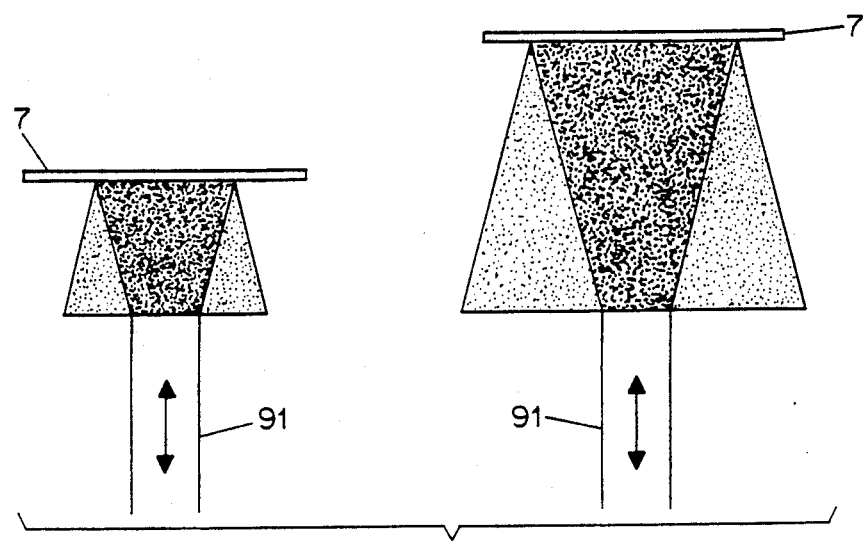
FIG. 10 shows the dispersion of light in a sensor such as that shown in FIG. 9.
Figure 10B:
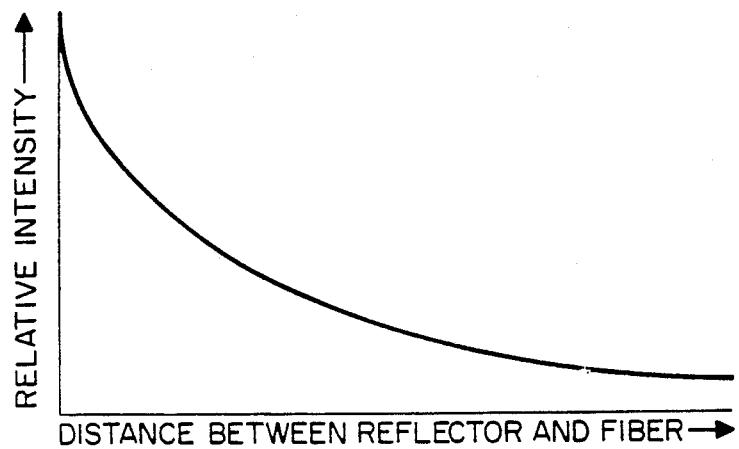

FIG. 9 shows a further embodiment of the invention in which a single optical fiber 91 is employed within the detector. The optical fiber 91 is joined to a second optical fiber 92 via an optical coupler 93, such as a beam splitter. Light travels from the source 94 through fiber 91 and is split by the coupler into two parts, one part of which travels through optical fiber 91 to the sensor and one part of which travels to a capped end. Reflected light from the sensor 95 is split passing back through the coupler 93 to detector element 96. FIG. 10 shows how light collection varies with distance between the reflector and the optical fiber.

The single fiber arrangement is desirable because it allows use of a smaller detector and because the geometry is simpler. On the other hand, inclusion of a beam splitter increases the cost of the device.

Miniaturization of the polymer sensing element is important to minimize response times and to avoid sample perturbation. Ideally, a sensor does not perturb the sample. In practice, however, a certain amount of analyte is required to interact with the sample to get a measurable response. If the amount of analyte required for a response is large relative to the total amount of analyte available in the sample, then the sensor will remove a significant fraction of the analyte from the sample, thus perturbing the sample. This situation is also subject to long response times due to the time required for mass transfer of the necessary amount of analyte to the sensor surface.

Because the sensors of the invention require a high concentration of analyte within the sensing element to generate a measurable response, they are quite likely to perturb the sample unless the sensor element itself is very small. Smaller polymeric detector elements also have faster response times. On the other hand, smaller polymeric detector elements have reduced sensitivities. Taking these factors into consideration, it is preferred to keep the size of the sensing element below about 1000 nanoliters. For some applications such as where the polymer has significant volume changes, the bead may advantageously have a volume of 1 nanoliter or smaller.

Specialized equipment to deliver volumes of 1 nanoliter or less has been developed for injecting foreign material into living cells. Ansorge, "Improved System for Capillary Microinjection into Living Cells", Exper. Cell Res., 140, 31 (1982). Such equipment is available commercially. Miller, "A Review of Microinjection and Micromanipulation Products", Amer. Biotechnol. Lab., Jan. 30, 1989. It includes a pipet puller for making small diameter pipets, a microinjector for reproducibly forcing out a small volume of solution through the small diameter pipet, and a micromanipulator for positioning the end of the pipet so that the solution is delivered to the appropriate location. The entire operation is observed under a microscope.

The reflective members in the sensors of the invention are made from light weight materials which can be readily deformed or moved in response to volume changes of the polymeric detector element. For example, the reflective member may be a thin piece of glass, such as a microscope cover slip, coated with metal to form a reflective surface. Other useful materials include shiny metals such as aluminum and stainless steel (specular reflectors) and diffuse reflectors such as magnesium sulfate coated surfaces.

The key element in the sensors of the invention is the polymeric detector element because it is the properties of the polymeric detector element which provide the sensitivity and selectivity of the sensor. Polymer swelling (or contraction) which forms the foundation of the invention occurs in both neutral and charged polymers. Thus, both neutral and charged particles can be used in forming the polymeric detector element.

1. Neutral Polymers

When a crosslinked polymer is placed in contact with a compatible solvent (e.g. crosslinked dextran in water or polystyrene in benzene), it will swell. If the polymer were not crosslinked, it would dissolve. Instead, however, it swells to an equilibrium point at which the free energy of mixing is just balanced by the elastic free energy needed to stretch the polymer network. This provides the basis for the thermodynamics of polymer swelling which are developed in the classic text by Flory, Principles of Polymer Chemistry, Cornell University Press (1953). The equation for swelling which comes out of this theory is given below:

$$q_m^{(5/3)} = (vM_c)(1-2M_c/M)(0.5-X_1)/v_1 \qquad (1)$$

where the terms are defined as follows:
  $q_m$ is the equilibrium swelling ratio, i.e. the volume of the swollen polymer at equilibrium divided by the volume of the unswollen polymer.
  $v$ is the specific volume of the polymer.
  $M_c$ is the molecular weight per crosslinked unit.
  $M$ is the molecular weight of the polymer prior to crosslinking.
  $X_1$ is a parameter expressing the first neighbor interaction free energy, divided by kT, for solvent with polymer. Selectivity of the polymer is embodied in this term.
  $v_1$ is the specific volume of the solvent.

The critical experimental parameter is the degree of crosslinking. The lower the degree of crosslinking, the higher the value of $M_c$ and the greater the degree of swelling. Note, however, that there must be a correction for loose chain ends in the network. This is embodied in the $(1-2M_c/M)$ term. To keep this term small, a polymer with a high molecular weight should be used.

The above equation is developed for a crosslinked polymer in contact with pure solvent. The situation of interest for the proposed sensing application is where an analyte is dissolved in a solvent. The polymer should be chosen to have a strong affinity for the analyte but not for the solvent. For example, crosslinked polystyrene might be chosen as the polymer for sensing benzene in water. In this context, the critical parameter is the chemical potential of the analyte. In a saturated solution, the analyte has the same chemical potential as it does in the pure state. For example, a saturated solution of benzene in water will swell crosslinked polystyrene to the same extent as pure benzene. Thus, the degree of swelling to be expected for a given analyte concentration will depend on the concentration of analyte relative to the saturation concentration.

The extent of polymer swelling can be quite large. Typically, the value of $q_m$ exceeds ten for a lightly crosslinked polymer, i.e. $M_c > 10,000$, in a good solvent. Crosslinked poly(vinyl alcohol) has $q_m$ values on the order of twenty in water.

Equation 1 does not show how swelling would vary as a function of analyte concentration. This has been considered elsewhere. J. Guillot, "Emulsion Copolymerization: Simulation of Particle Morphology," in Future Directions in Polymer Colloids," p. 65 (1987). The relevant equation is:

$$\ln a_i = \{\ln(1-\phi_p)+\phi_p+X_i\phi_p^2\}+(K/M_c)(\phi_p^{1/3}-0.5\phi_p) \qquad (2)$$

where $\phi_p$ is the volume fraction of polymer, K is a constant, and $a_i$ is the activity of species i. The other terms are defined as before. As activity approaches unity, $\phi_p$ decreases. This corresponds to a large volume fraction of species i in the polymer ($\phi_i = 1-\phi_p$, where $\phi_i$ is the volume fraction of i n the polymer), i.e. a higher degree of swelling.

2. Ionic Polymers

Electrostatic repulsion between like charges on an ionic polymer can greatly increase swelling forces. The magnitude of the repulsion depends on the number of charges and on the concentration of counterions which are inevitably present in the polymer. Increasing counterion concentration causes an increase in charge shielding, resulting in a decrease in repulsive forces.

This can also be viewed as an osmotic pressure effect. The ion concentration within the crosslinked polymer is higher than it is in the solvent. Consequently, solvent enters the polymer attempting to equalize the ion concentration inside and outside the polymer.

The theory of swelling of ionic polymers is treated by Flory, who derives the approximate equation:

$$q_m^{(5/3)} = [(i/2v_u s)^2 + (0.5-x_1)/v_1]/(v_e/V_o) \qquad (3)$$

where the new terms are defined as follows:
  i is the number of charges per repeating polymer unit
  $v_u$ is the volume of a repeating polymer unit
  S is the ionic strength
  $v_e$ is the effective number of chains in a real network
  $V_o$ is the volume of the unswollen polymer network The second term in equation (3) is another form of equation (1) and accounts for the swelling of the polymer due to interaction with solvent. The first term accounts for the electrostatic effects. The electrostatic component of swelling depends on two parameters: the charge density, $i/v_u$, and the ionic strength, S.

Because swelling of charged polymers depends on ionic strength, a polymer with a fixed charged density can be used in a system to optically sense ionic strength. A polymer bead with the desired charge density can be obtained by chemically varying the number of charges on the polymer. For example, for poly(methacrylic acid) crosslinked with divinyl benzene, the charge density may be controlled by adding known amounts of NaOH to partially neutralize the carboxylic acid groups. Katchalsky et al., J. Polymer Sci., 7, 571 (1951). Swelling ratios as high as 500 have been observed with 1% crosslinking.

In order to take advantage of this swelling behavior in a sensor for more specific analytes, however, the polymer must have an affinity for the target analyte. This can be achieved by selection of polymers or modification of non-selective polymers. Suitable polymers include polyvinylalcohol, polyethyleneimine, and polyacrylamide, polystyrene, crosslinked dextran and polyacrylic acid. Modifiers include chelating ligands, crown ethers, cyclodextrins and other size selective hosts for organic compounds, and unsaturated metal complexes that coordinate to neutral molecules and anions. Modifiers also may be biomolecules.

Polyvinyl alcohol (PVOH) can be crosslinked with glutaraldehyde to yield a polymer useful in sensors of the present invention. As noted in Zhujun et al., Anal. Chem., 61, 202 (1989), a 5% (w/w) solution of aqueous polyvinyl alcohol can be crosslinked with glutaraldehyde in the presence of HCl. The amount of HCl is preferably chosen such that it takes about 5 minutes for a gel to form, as this allows time for transferring the material into the sensor before solidification. If an etched silica support is used as shown in FIG. 7, the surface of the support is advantageously functionalized with aldehyde groups to facilitate binding of PVOH.

This can be accomplished using 3-glycidolylpropyl)-trimethoxysilane followed by periodate as shown in the following reaction scheme:

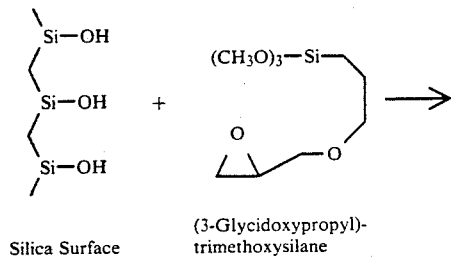

Silica Surface    (3-Glycidoxypropyl)-trimethoxysilane

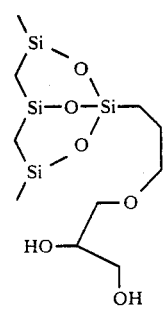

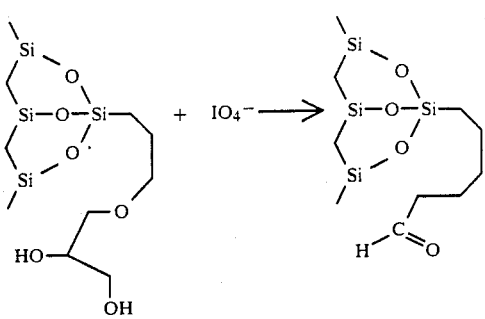

Unmodified PVOH can be used in a sensor according to the invention for detecting water in organic solvents such as toluene, hexane and methylene chloride. Further, PVOH can be used as a substrate for immobilizing reagents for ion detection. For example, N-(2-hydroxyethyl)ethylenediaminetriacetic acid (HEDT) may be used as a ligand for detecting trace metal ions based on polymer swelling. An appropriate polymer is prepared via a cyanuric chloride-HEDT conjugate by reacting equimolar amounts of the two reagents in acetone, removing the acetone, and reacting the resulting product directly with aqueous PVOH (14,000 MW, 100% hydrolyzed) as shown:

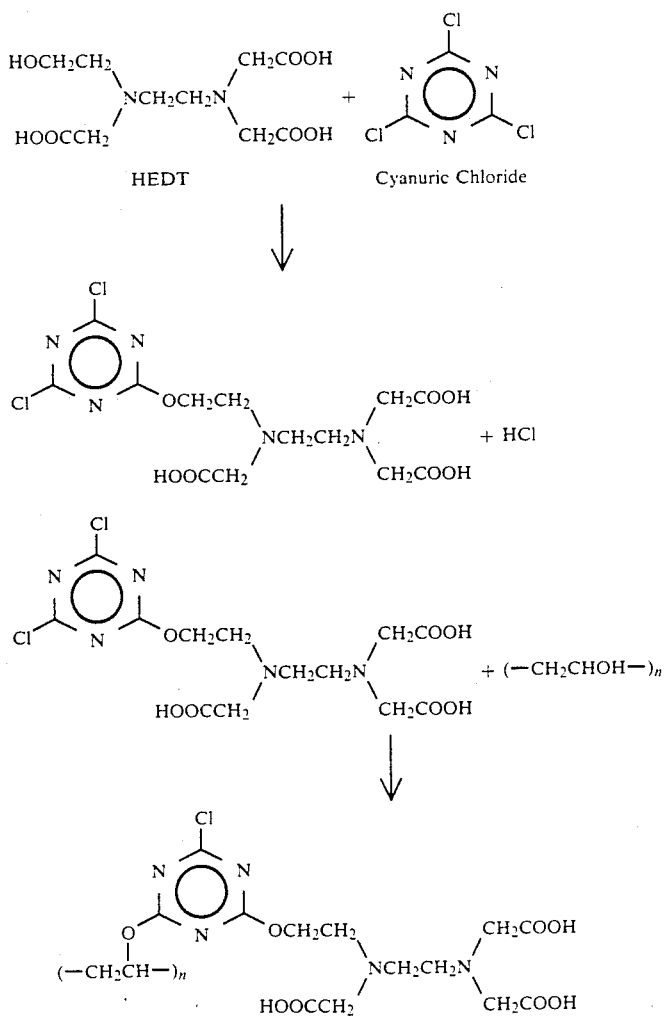

After removing excess reagent by dialysis, the amount of immobilized HEDT may be determined by a potentiometric titration with Cu(II), followed with a Cu(II) electrode. These procedures are similar to those described in Zhujun et al., "Poly (vinyl alcohol) as Substrate for Indicator Immobilization for Fiber Optic Chemical Sensors", Anal. Chem., 61, 202 (1989); and Dowling et al., "Binding of Sulfonated Fluorophors by Metal-Polyethyleneimine Complexes", Macromolecules, 19, 344 (1986). The HEDT/PVOH conjugate is then crosslinked with glutaraldehyde as described above.

In addition to being readily immobilized, HEDT is advantageous because it is a well-characterized ligand with known pKa's and formation constants. Martell et al., in "Critical Stability Constants", Volume 1, Plenum Press, N.Y., p. 199 (1974). HEDT forms 1:1 complexes with metal ions avoiding potential complications associated with formation of 2:1 and higher complexes. The change in charge accompanying metal ion binding depends on the charge on the metal ion and the number of ions displaced during the binding process. Assuming that immobilization does not significantly affect the acid-base properties of HEDT, it should be monoprotonated over the pH range between 6 and 9 with a net charge of minus two. Reaction with a divalent metal ion will lead to a complex with a charge of minus one and thus be accompanied by shrinking of the polymer. Reaction with a trivalent metal, e.g. Fe(III), will lead to a neutral complex and thus be accompanied by an even larger degree of shrinkage. Thus, different types of charge shifts will accompany metal ion binding and can be used as an indicator of the quality and quantity of metal ions present.

It is anticipated that the sensor will respond to a range of concentrations centered around the point where pM = log Kf' (analogous to pH sensors responding to concentrations centered around the pKa) where Kf' is the conditional equilibrium constant for metal ion binding. We also anticipate that immobilization will lead to a distribution of Kf' values and that this will be reflected in the response curve.

Because HEDT is a pentadentate ligand, Kf' values are quite large even at relatively low pH. Accordingly, this is a system where there will be a large preconcentration factor in the polymer. Therefore, this is an example of a system where it is important to minimize the size of the polymer.

PVOH can also be used to immobilize macrocyclic ionophores which provide a high degree of selectivity based on the size of the macrocycle cavity for use in sensors according to the invention. For example, benzo-15-crown-5 can be incorporated in a PVOH polymer by converting it to an amino derivative. Feigenbaum et al., "Novel Polyamides from Macro-Cyclic Ethers", J. Poly. Sci., Part Al, 9, 817 (1971); and Ungaro et al., "Substituent Effects on the Stability of Cation Complexes of 4'-Substituted Monobenzo Crown Ethers", J. Amer. Chem. Soc., 98, 5198 (1976). The first step is to introduce a nitro group on the benzene ring. Catalytic hydrogenation converts this to an amino group as shown:

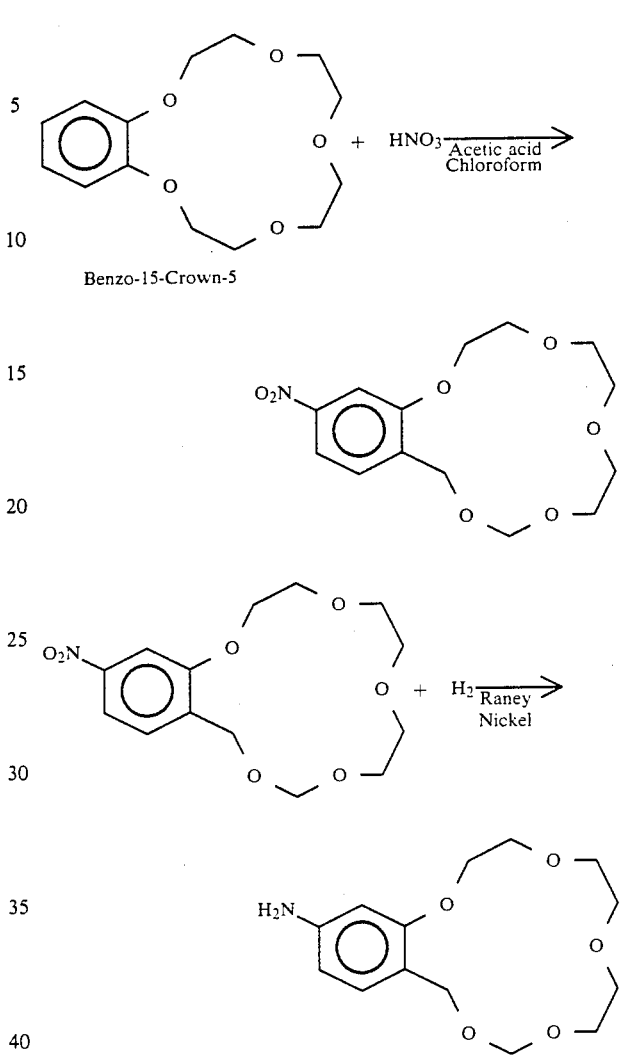

Benzo-15-Crown-5

Once the aminobenzo-15-crown-5 has been prepared, the procedure is parallel to that discussed above for HEDT. The cyanuric chloride derivative of aminobenzo-15-crown-5 is prepared and reacted with PVOH. The amount of immobilized ligand may be determined by UV spectrophotometry.

The aminobenzo-15-crown-5 system is inherently simpler than HEDT because the ligand is neutral at all pHs and complexation does not involve displacement of a proton. It is anticipated that the alkali metal ions will cause the polymer to swell. Formation constants in water are extremely small (approximately 2.5 for both sodium and potassium), however, and thus these measurements are preferably conducted in 2:3 methanol:water. In this medium, the log Kf's for formation of the potassium and sodium complexes are 1.17 and 1.92 respectively. Izatt et al., "Thermodynamic and Kinetic Data for Cation-Microcycle Interaction", Chem. Rev., 85, 271 (1985).

Another polymer which can be used in sensors according to the invention is polyethyleneimine (PEI). This is more difficult because PEI generally crosslinks rapidly and therefore it is difficult to establish conditions under which the polymer can be manipulated as a liquid. It has been found, however, that PEI can be crosslinked slowly enough so that crosslinking indicator-PEI conjugate can be manipulated as a liquid using dimethyl adipimidate (DMA) as a crosslinking reagent. Preferably solid DMA is added to 10% aqueous PEI to take DMA hydrolysis into account.

To covalently bond PEI to the sensor, the glass and silica surfaces can be reacted with 3-aminopropyltriethoxysilane to form amine groups on the surface as shown:

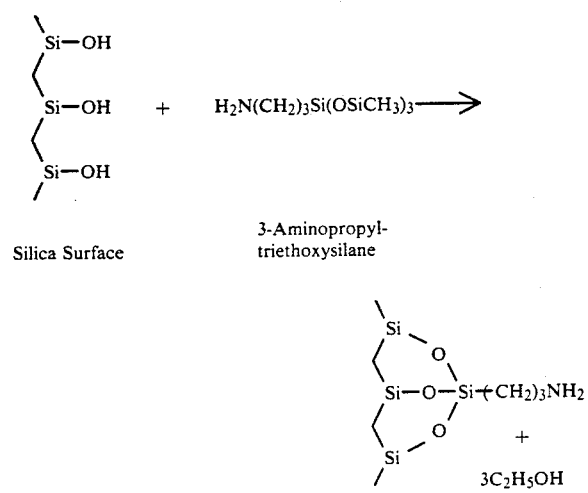

Silica Surface     3-Aminopropyl-triethoxysilane

PEI is a desirable polymer because (1) it is amenable to more immobilization chemistries than PVOH because amine groups are more reactive than hydroxy groups and (2) it can be used to immobilize biomolecules and other reagents that are not stable at the low pH required for crosslinking PVOH with glutaraldehyde. However, unlike PVOH, PEI is intrinsically sensitive to pH because amine groups can be protonated. This means PEI may be useful as a pH indicator, but also that pH will have to be considered in standardizing other PEI-based detector systems.

Another complication is that PEI forms strong complexes with metal ions like Cu(II). Martell et al., in "Critical Stability Constants", Volume 1, Plenum Press, N.Y. p. 199 (1974). Because crosslinking will reduce the flexibility of the polymer chains, it may reduce the affinity for Cu(II).

Another class of polymers for use in the inventions are cyclodextrins. Cyclodextrins are cycloamyloses containing a variable number of glucose units. $\alpha$-, $\beta$- and $\gamma$- are the most common cyclodextrins, containing 6,7 and 8 glucose units respectively. These molecules have attracted great interest because the hydroxyl groups are oriented outward leaving a hydrophobic interior capable of binding lipophilic molecules that fit in the cavity, while rejecting larger molecules. Bender et al., "Cyclodextrin Chemistry", Springer Verlag, Berlin (1978). The size of the cavity increases with the number of glucose units in the ring. Thus, cyclodextrins provide a family of binding reagents that are selective based on "guest" size.

Uncomplexed cyclodextrins are highly water soluble. Their complexes have much lower water solubilities. Table 1 reproduces values from the literature to provide an appreciation of the magnitude of the solubility changes accompanying complexation. See, Cramer et al., "Gesetzmassigkeiten bei der Bildung von Addukten der Cyclodextrine", Chem. Ber., 90, 2561 (1957). Since crosslinked polymers swell due to solvation, it is anticipated that complexation would reduce the extent to which a crosslinked cyclodextrin polymer swells. Therefore, it is expected that crosslinked cyclodextrin polymers will serve as sensing elements that are selective on the basis of size.

TABLE 1

| Complexing Forming Reagent | Cyclodextrin Derivative | | |
|---|---|---|---|
| | $\alpha$ | $\beta$ | $\gamma$ |
| None | 12.0 | 1.48 | 22.0 |
| Fluorobenzene | 1.14 | 0.00 | 1.60 |
| Chlorobenzene | 1.32 | 0.00 | 0.36 |
| Benzene | 1.24 | 0.075 | 0.3 |
| Cyclohexane | 0.22 | 0.13 | 1.63 |
| Biphenyl | 5.7 | 0.47 | 2.97 |

Solubility of Cyclodextrins in the Presence and Absence of Complexing Forming Reagents All solubilities are in g/100 ml at 25° C.

Cyclodextrins have been crosslinked with epichlorohydrin yielding gels that swell in water. Solms et al., "Harze mit Einschlusshohl Raumen von Cyclodextrin—Struktur", Helv. Chem. Acta, 48, 1225 (1965); and Hoffman "Chromatography of Nucleic Acids on Crosslinked Cyclodextrin Gels Having Inclusion—Forming Capacity", J. Macromol. Sci. Chem., A7, 1147 (1973). Gels formed in this manner are available commercially from American Maize Products Company. However, use of the same glutaraldehyde crosslinking procedure developed for PVOH is preferred, because this allows the rate of crosslinking to be controlled. As with PVOH, covalent bonding to the sensor will be accomplished by modifying the glass surfaces to form aldehydes.

Because cyclodextrins are relatively small, a high degree of crosslinking will be necessary to form an insoluble gel. An alternative is to combine PVOH and cyclodextrins to form a mixed gel. The potential advantage of such an approach is that a lower concentration of crosslinker can be added because PVOH has a higher molecular weight such that fewer crosslinks are required to form an insoluble network. The disadvantage is that the cyclodextrin "concentration" in the crosslinked polymer will be diluted by the PVOH.

T-butyl polystyrene can be used to detect hydrocarbons such as oil or gasoline in water. To prepare the polymeric detector element, tertiary-butyl styrene (available from Polysciences, Inc.) is combined with divinylbenzene, a crosslinking reagent, and benzoyl peroxide, an initiator. This solution is heated to induce polymerization. Beads are prepared by suspending the mixture in vigorously stirred aqueous solution. A drop of known volume is transferred to an end of the fused silica fiber which has been cleaned and reacted with vinyltrichlorosilane so that it will covalently couple to the crosslinked t-butyl-polystyrene. The reflector may be similarly treated if binding to the reflector is desired.

T-butylpolystyrene should undergo a volume change in response to the concentration for benzene, toluene, hexane and other hydrocarbons in water making it a useful detector. Based on results described in Turner, "The Swelling of Polymer Gels", MS. Thesis, University of New Hampshire (1986) it is anticipated that the response will depend on percent saturation.

Sensors according to the invention may also include a biomolecule that selectively interacts with the analyte. The requisite condition is that the interaction between the analyte and biomolecule must affect the extent of polymer swelling. This can be achieved when the biomolecule is a catalyst, most likely an enzyme. It could also be a catalytic antibody or some other type of biological catalyst. In this case the chemical reaction that is selectively catalyzed involves formation of a product which affects the extent to which a polymer swells or shrinks.

One example would be a penicillin sensor. The sensing element would be the enzyme penicillinase bound to a pH-sensitive polymer. Penicillinase catalyzes the reaction of penicillin to form penicillinoic acid. This reaction is accompanied by a change in pH which will cause the polymer to shrink or swell.

Another example would be a urea sensor. The sensing element would be immobilized urease on a substrate that would swell or shrink with changes in ammonia concentration. Interaction with urea would change the ammonia concentration which would affect the degree of polymer swelling.

Sensors can also involve bioreceptors such as antibodies or cell surface receptors that selectively bind analyte but do not catalyze a reaction. The sensing element would involve the bioreceptor covalently bound to a swellable polymer matrix. The binding process itself might cause the polymer to swell. In this case direct detection of the analyte is possible.

Another approach is to base detection on competitive binding, i.e. the displacement of a labelled analyte analogue by the analyte. The extent of displacement will vary with analyte concentration. The label can be a chemical that directly or indirectly affects the swelling of the polymer. For example, the label could be an enzyme that catalyzes a reaction that causes a change in pH. The polymer would sensitive to pH and would swell or shrink as the pH changed.

EXAMPLE 1

An ionic strength sensor configured as shown in FIG. 1 was prepared using a sulfonated crosslinked dextran bead (C-50-120 SP-Sephadex) as the detector element. The diameter of the bead was 120 μm as supplied and 400 μm when fully swollen with water.

Separate plastic clad fused silica optical fibers with 200 micrometer core diameters (from Ensign-Bickford, Inc.) were used to conduct light to and from the reflecting surface. The fiber was surrounded by a plastic buffer such that the total diameter was 500 micrometers. The two fibers were touching each other. Therefore, the distance between the two fiber cores was 300 micrometers. The fibers were held together in an SMA style fiber optic connector. The hole in the connector was drilled out to be larger so that it could accommodate two optical fibers.

The light source and the detection system were parts of an SLM 8000 spectrofluorometer. The light source was a 450 watt xenon arc lamp. This radiation passed through a double monchromator before it was focussed into the optical fiber conducting light to the reflector. A specially machined aluminum adapter was prepared so that light from the spectrofluorometer could be coupled into an optical fiber with an SMA style fiber optic connector.

The reflector for these measurements was a small strip of shiny metal. It was held in place by the elastic material from the reinforced toe of a pair of panty hose. This elastic material was attached to three hooks positioned around the reflector.

The sensor was immersed in solutions of KCl, NaCl or $Na_2SO_4$ of varying molarity. The intensity of the reflected light was measured following a period of equilibration of 30 to 70 seconds using the photomultiplier tube used in the SLM 8000 spectrofluorometer.

Figure 11:
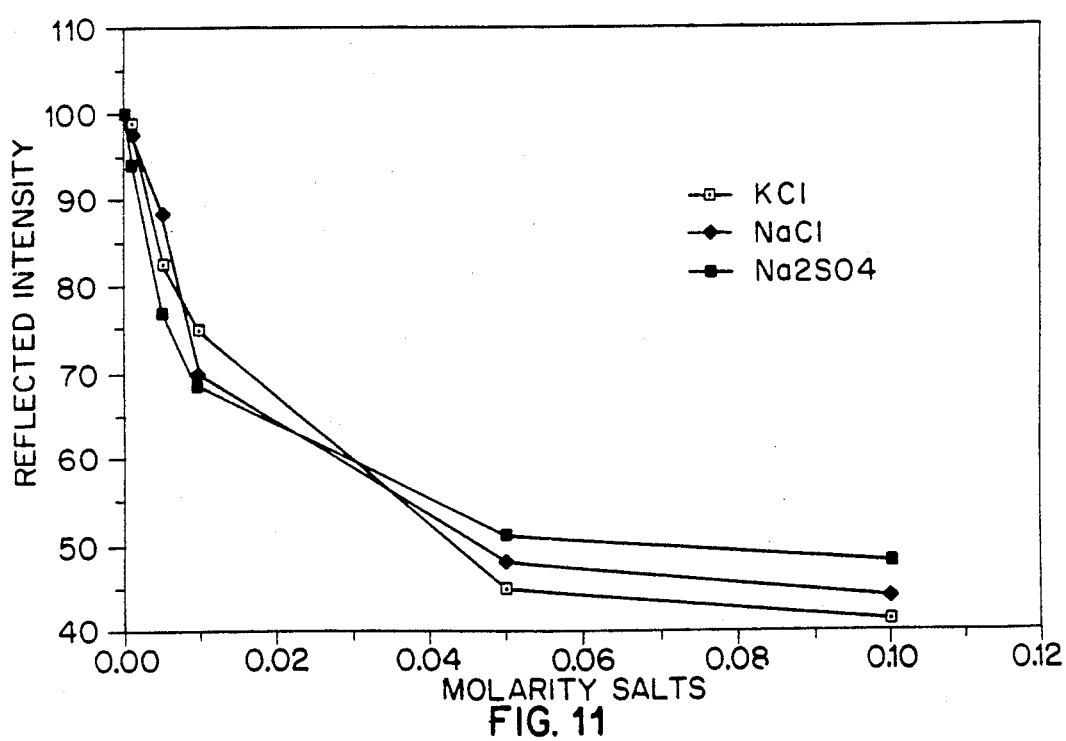
FIG. 11 is a graph depicting relative reflected intensity as a function of salt concentration.

Measurements were made with incident light at 400 nm and 500 nm. The absolute intensities were different at the two wavelengths. However, the relative change in intensity as a function of added analyte was the same within experimental error for the two wavelengths. The results are shown in FIG. 11.

EXAMPLE 2

Figure 12:
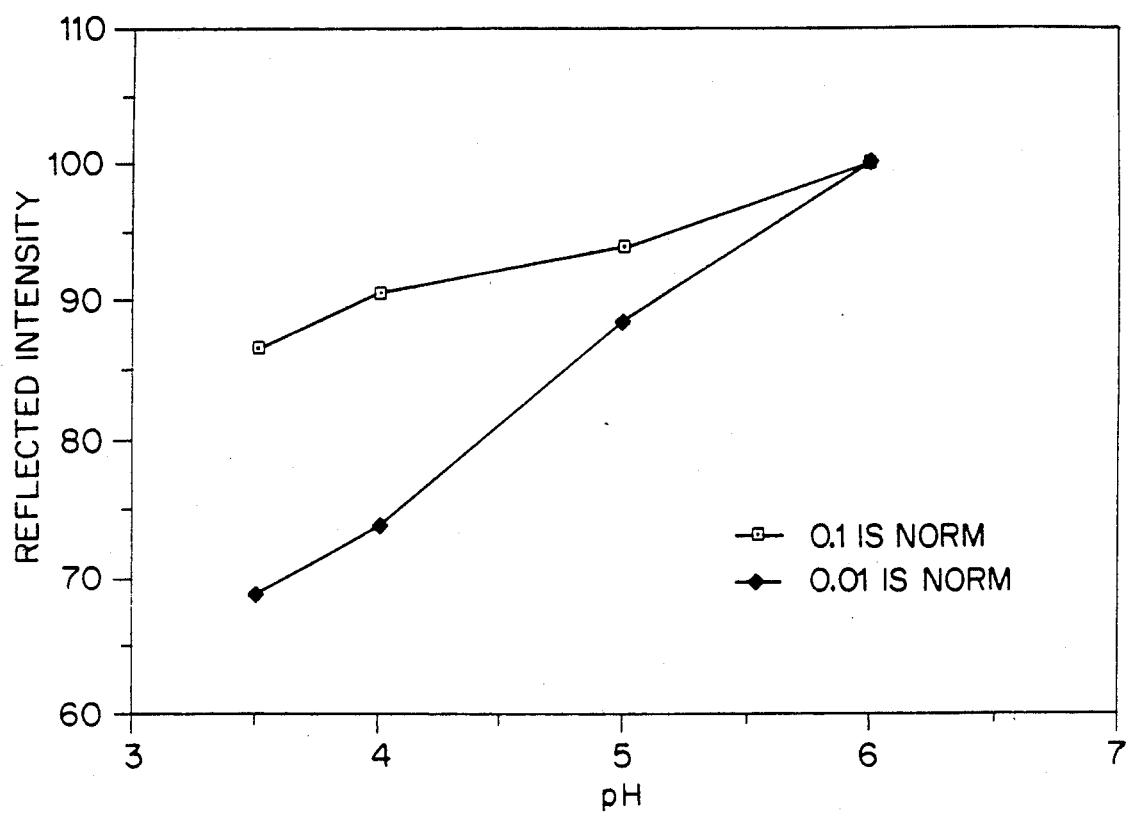
FIG. 12 is a graph depicting relative reflected intensity as a function of pH at 0.10 and 0.010M ionic strength.

A pH sensor was constructed as shown in FIG. 1 using a carboxylated crosslinked dextran bead (C-50-120 CM-Sephadex) of approximately the same size as the SP-Sephadex bead of Example 1 as the detector element. The light intensities observed at different pHs are shown in FIG. 12.

Data are presented for two different salt concentrations to show how response is affected by ionic strength. Relative intensity changes are on the order of 10% for a pH change of 1.0 unit. If the source is stable to 1 part in 10,000, this means that a change of 0.001 pH unit can be detected. With temperature control, stabilities considerably better than 1 part in 10,000 have been achieved with an LED. Smith et al., "High Precision Fluorimetry With a Light Emitting Diode Source", Appl. Spec. 42, 1469 (1988).

As will be understood from the foregoing description and examples, the sensors of the invention offer a new approach to the detection and quantification of analytes. The sensors can be used in connection with diverse analytes, ranging from ions generally (ionic strength) and pH to specific biomolecules, by selecting a polymeric sensing element with the desired specificity. Furthermore, while the examples describe detection of analytes in solution, the sensors can also be employed to detect analytes in gases, for example humidity and the presence of hydrocarbons and chlorinated hydrocarbons in air.

The sensors of the invention provide stable, rugged devices for the detection of various analytes. Because the detector element is a crosslinked polymer, it is not subject to leaching or photodecomposition. Moreover, the heat sensitivity of polymers is generally much lower than that of other systems.

The sensors of the invention can be used in numerous applications and environments. For example, because of the ability to use the wavelengths of light used in communications application (e.g. LED sources), the light in the detector can be transmitted for distances of a kilometer or more. This means that the light source and detector can be kept under stable environmental conditions, remote from the sample being monitored, thus improving both the performance and the longevity of equipment.

We claim:

1. A detector for quantifying an analyte in a sample comprising:
   (a) a housing
   (b) light transmission means disposed within the housing such that light can be transmitted in both directions through the housing;
   (c) means for coupling a first end of the light transmission means to a light source;
   (d) means for coupling the first end of the light transmission means to a photodetector;

(e) a reflective member movable between first and second positions with respect to the light transmission means wherein the reflective member is disposed adjacent to a second end of the light transmission means such that light transmitted through the light transmission means from the first end to the second end is reflected by the reflective member and at least partially recollected by the light transmission means and wherein the amount of light recollected depends on the position of the reflective member relative to the light transmission means; and (f) a polymeric detector element the volume of which varies in response to the amount of analyte in the sample, said detector element being mechanically connected to the reflective member and the light transmission means such that the position of the reflective member relative to light transmission means depends on the volume of the detector element.

2. A detector according to claim 1, wherein the light transmission means comprises one or more optical fibers.

3. A detector according to claim 1, wherein the polymeric detector element comprises a polymeric material selected from the group consisting of polyvinyl alcohol, polyethyleneimine, polyacrylamide, polystyrene, crosslinked dextran and polyacrylic acid.

4. A detector according to claim 1, wherein the polymeric detector element is modified with a material selected from among chelating ligands, crown ethers, cyclodextrins, metal complexes that coordinate neutral molecules or anions, antibodies, bioreceptors and catalytic biomolecules.

5. A detector according to claim 3 wherein the polymeric detector element is modified with a material selected from among chelating ligands, crown ethers, cyclodextrins, metal complexes that coordinate neutral molecules or anions, antibodies and catalytic biomolecules.

6. A detector according to claim 1, wherein the polymeric detector element comprises polyvinyl alcohol crosslinked with glutaraldehyde.

7. A detector according to claim 1, wherein the polymeric detector element comprises polyethyleneimine.

8. A detector according to claim 2, wherein the light transmission means is a single optical fiber.

9. A detector according to claim 8, wherein the detector further comprises an optical coupler.

10. A detector according to claim 9, wherein the polymeric detector element is covalently bonded to the housing.

11. A detector according to claim 9, wherein the reflective member is affixed to a support which engages slidably with the housing.

12. A detector according to claim 9, wherein the optical fiber, the reflective member and the polymeric detector element are disposed sequentially within a common bore in the housing, further comprising a rigid support disposed across the bore in contact with the side of polymeric detector element remote from the reflective member, wherein the rigid support allows the passage of sample and serves to mechanically couple the polymeric sensing element to the optical fiber.

13. A detector according to claim 9, further comprising a light source.

14. A detector according to claim 13, wherein the light source is a light emitting diode.

15. A detector according to claim 9, wherein the polymeric sensing element has a volume of less than about 1000 nanoliters.

16. A detector according to claim 2, wherein the light transmission means comprises two optical fibers.

17. A detector according to claim 16, wherein the polymeric detector element is covalently bonded to the housing.

18. A detector according to claim 16, wherein the reflective member is affixed to a support which engages slidably with the housing.

19. A detector according to claim 16, wherein the optical fiber, the reflective member and the polymeric detector element are disposed sequentially within a common bore in the housing, further comprising a rigid support disposed across the bore in contact with the side of polymeric detector element remote from the reflective member, wherein the rigid support allows the passage of sample and serves to mechanically couple the polymeric sensing element to the optical fiber.

20. A detector according to claim 16, further comprising a light source.

21. A detector according to claim 20, wherein the light source is a light emitting diode.

22. A detector according to claim 16, wherein the polymeric sensing element has a volume of less than about 1000 nanoliters.

23. A detector according to claim 1, wherein the distance between the reflective member and the light transmission means can be varied independent of the volume of the polymeric detector element.

24. A detector according to claim 1, wherein the light transmission means comprises at least two optical fibers, the second ends of said optical fibers being disposed at different distances from the reflective member.

25. A detector according to claim 24, further comprising a light source.

26. A detector according to claim 2, wherein the light transmission means comprises at least three optical fibers, said fibers being disposed such that the center-to-center difference between a first of said optical fibers and a second of said optical fibers is different from the distance between the first of said optical fiber and a third of said optical fibers.

27. A detector according to claim 26, further comprising a light source.

28. A method for detecting an analyte in a sample, comprising (a) contacting the sample with a detector comprising a polymeric detector element, the volume of which depends on the amount of the analyte, a light transmission means and a reflector, arranged such that the light transmitted through the light transmission means is reflected by the reflector and recollected by the light transmission means to an extent determined by the volume of the sensing element being in contact with the sample for a period of time sufficient for the sensing element to come to its equilibrium volume;

(b) introducing light through the light transmission means;

(c) measuring the intensity of the light reflected and recollected by the light transmission means; and (d) comparing the reflected intensity with a standard to determine the amount of analyte.

29. A method according to claim 28, wherein the light transmission means comprises one or more optical fibers.

30. A method according to claim 28, wherein the light transmission means comprises at least two optical fibers disposed at different distances from the reflective member, and wherein two intensities of reflective light are measured further comprising the step of determining the ratio of the measured intensities for comparison to the standard.

* * * * *